(12) United States Patent
Donde et al.

(10) Patent No.: US 7,863,319 B2
(45) Date of Patent: *Jan. 4, 2011

(54) CYCLOPENTANE HEPTAN(ENE)OIC ACID, 2-HETEROARYLALKENYL DERIVATIVES AS THERAPEUTIC AGENTS

(75) Inventors: Yariv Donde, Dana Point, CA (US); Robert M. Burk, Laguna Beach, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/623,417

(22) Filed: Jan. 16, 2007

(65) Prior Publication Data

US 2007/0112051 A1    May 17, 2007

Related U.S. Application Data

(63) Continuation-in-part of application No. 10/915,933, filed on Aug. 10, 2004, now Pat. No. 7,183,310.

(51) Int. Cl.
*A61K 31/381* (2006.01)
*C07D 333/28* (2006.01)

(52) U.S. Cl. ............... 514/438; 549/78; 549/79; 549/80

(58) Field of Classification Search ............. 548/78; 514/438; 549/78, 79, 80
See application file for complete search history.

(56) References Cited

U.S. PATENT DOCUMENTS

| | | | | |
|---|---|---|---|---|
| 4,055,602 A | 10/1977 | Nelson | .................. | 250/613 D |
| 4,119,727 A | 10/1978 | Buendia et al. | ............ | 424/275 |
| 4,166,452 A | 9/1979 | Generales, Jr. | .............. | 128/741 |
| 4,256,108 A | 3/1981 | Theeuwes | ................... | 128/260 |
| 4,265,874 A | 5/1981 | Bonsen et al. | ................ | 424/15 |
| 4,994,274 A | 2/1991 | Chan et al. | ................. | 424/427 |
| 5,028,624 A | 7/1991 | Chan et al. | ................. | 514/530 |
| 5,034,413 A | 7/1991 | Chan et al. | ................. | 514/530 |
| 5,446,041 A | 8/1995 | Chan et al. | ................. | 514/530 |
| 6,124,344 A | 9/2000 | Burk | ......................... | 514/438 |
| 7,183,310 B2 * | 2/2007 | Donde et al. | ................ | 514/438 |

FOREIGN PATENT DOCUMENTS

| | | |
|---|---|---|
| DE | 2626888 | 4/1977 |
| DE | 2719244 | 11/1977 |
| EP | 0283151 A2 | 9/1988 |
| GB | 1601994 | 4/1978 |
| JP | 53135955 | 11/1978 |
| WO | WO/90/02553 | 3/1990 |
| WO | WO/94/06432 | 3/1994 |
| WO | WO 95/11682 | 5/1995 |
| WO | WO 95/26729 | 10/1995 |
| WO | WO 99/25358 | 5/1999 |

OTHER PUBLICATIONS

Bito, L.Z. *Biological Protection with Prostaglandins*, Cohen, M.M., ed., Boca Raton, Fla, CRC Press Inc., 1985, pp. 231-252.
Bito, L.Z., *Applied Pharmacology in the Medical Treatment of Glaucomas* Drance, S.M. and Neufeld, A.H. eds., New York, Grune & Stratton, 1984, pp. 477-505.
Bito, L.Z., *Arch. Ophthalmol. 105*, 1036 (1987).
Francis A. Carey, Organic Chemistry, New York: McGraw-Hill Book Company 1987, p. 63.
Nilsson et. al., *Invest. Ophthalmol. Vis. Sci.* (suppl), 284 (1987).
Remington's Pharmaceutical Science's, Mack Publishing Company, Easton, Pa., 16th Edition, 1980.
Siebold et al., *Esterified Prostaglandin Shows 'Potent' Promise*, Ocular Surgery News, vol. 1, No. 3 (Feb. 1989); pp. 3, 59.

* cited by examiner

*Primary Examiner*—Rebecca L Anderson
*Assistant Examiner*—Jason M Nolan
(74) *Attorney, Agent, or Firm*—Kevin J. Forrestal; John E. Wurst; Doina G. Ene

(57) ABSTRACT

A compound comprising

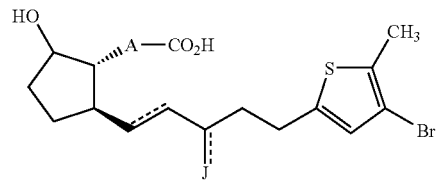

or a pharmaceutically acceptable salt or a prodrug thereof, having the groups described in detail herein is disclosed.

Figure 1:
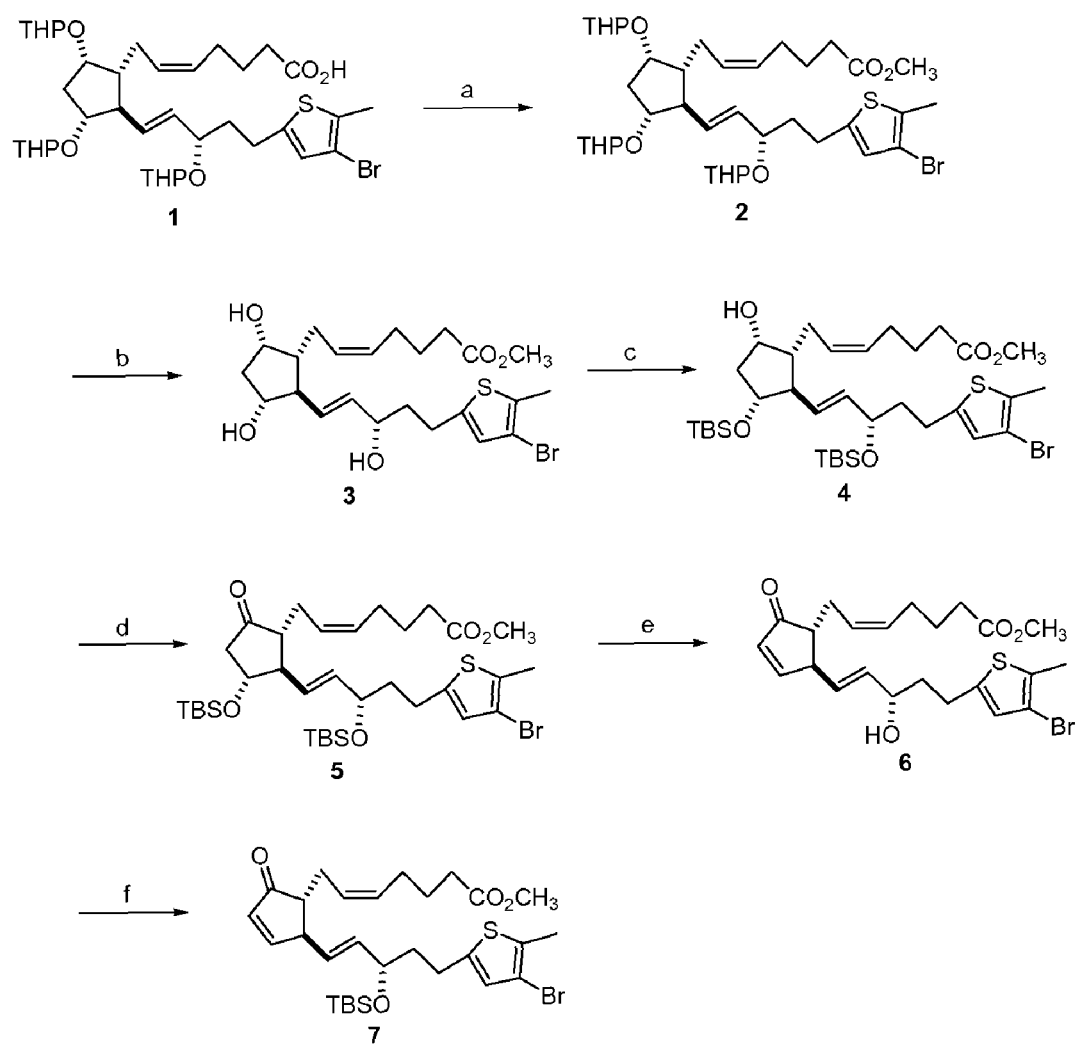

Also disclosed herein are compounds comprising

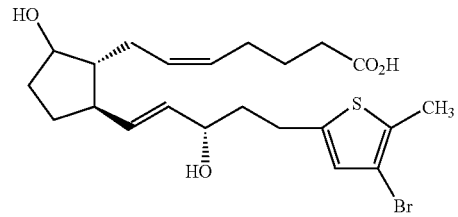

or derivatives thereof, or pharmaceutically acceptable salts, tetrazoles, or prodrugs of compounds of the structure or derivatives thereof, said derivatives being described in detail herein.

Also disclosed herein are methods of treating diseases or conditions, including glaucoma and elevated intraocular pressure. Compositions and methods of manufacturing medicaments related thereto are also disclosed.

4 Claims, 2 Drawing Sheets

(a) MeI, DBU, acetone; (b) PPTs, MeOH; (c) TBSCl, Et₃N, DMAP, CH₂Cl₂; (d) TPAP, NMO, 4A MS CH₂Cl₂; (e) HOAc, THF, H₂O 70 °C; (f) TBSOTf, 2,6-lutidine, CH₂Cl₂.

(a) [PhP$_3$CuH]$_6$; (b) NaBH$_4$, MeOH (ca. 1:1 diastereomers); (c) HOAc, THF, H$_2$O 70 °C; separate C9 diastereomers; (d) 0.5 M LiOH, THF.

CYCLOPENTANE HEPTAN(ENE)OIC ACID, 2-HETEROARYLALKENYL DERIVATIVES AS THERAPEUTIC AGENTS

CROSS-REFERENCE TO RELATED APPLICATIONS

This patent application is a continuation in part of U.S. patent application Ser. No. 10/915,933, filed Aug. 10, 2004, now U.S. Pat. No. 7,183,310, and claims priority thereto under 35 U.S.C. §120.

FIELD OF THE INVENTION

This invention relates to compounds which are useful as therapeutic agents. Among other potential uses, these compounds are believed to have properties which are characteristic of prostaglandins.

BACKGROUND OF THE INVENTION

Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

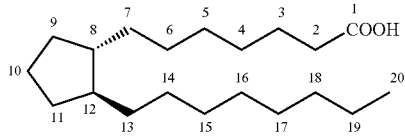

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231-252; and Bito, L. Z., *Applied Pharmacology in the Medical Treatment of Glaucomas* Drance, S. M. and Neufeld, A. H. eds., New York, Grune & Stratton, 1984, pp. 477-505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et. al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105, 1036 (1987), and Siebold et al., Ocular Surgery News 1989 February 1; 7(3):3,31].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of United States patents assigned to Allergan, Inc. prostaglandin esters with increased ocular hypotensive activity accompanied with no or substantially reduced side-effects are disclosed. Some representative examples are U.S. Pat. No. 5,446,041, U.S. Pat. No. 4,994,274, U.S. Pat. No. 5,028,624 and U.S. Pat. No. 5,034,413 all of which are hereby expressly incorporated by reference.

GB 1,601,994 discloses compounds having the formula shown below

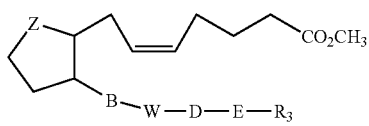

in which A represents a CH=CH group;

B represents a —CH2-CH2-, trans-CH=CH— or —C≡C— group,

W represents a free, esterified or etherified hydroxymethylene group, wherein the hydroxy or esterified or etherified hydroxy group is in the- orA-configuration, . . . or W represents a free or ketalised carbonyl group, D and E together represent a direct bond, or D represents an alkylene group having from 1 to 5 carbon atoms or a —C≡C—group, and E represents an oxygen or sulphur atom or a direct bond, $R_3$ represents an aliphatic hydrocarbon radical, preferably an alkyl group, which may be unsubstituted or substituted by a cycloalkyl, alkyl substituted cycloalkyl, unsubstituted or substituted aryl or heterocyclic group, a cycloalkyl or alkyl-substituted cycloalkyl group, or an unsubstituted or substituted aryl or heterocyclic group, e.g. a benzodioxol-2-yl group, and Z represents a free or ketalised carbonyl group or a free esterified or etherified hydroxymethylene group in which the free, esterified or etherified hydroxy group may be in the α- or β-configuration.

JP 53135955 discloses several compounds such as the one shown below.

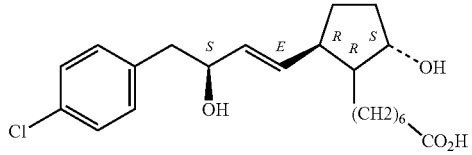

DE 2719244 discloses several compounds such as the ones shown below.

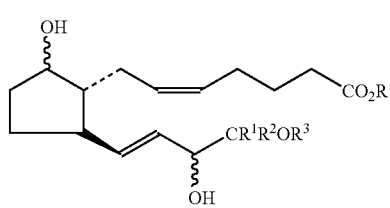

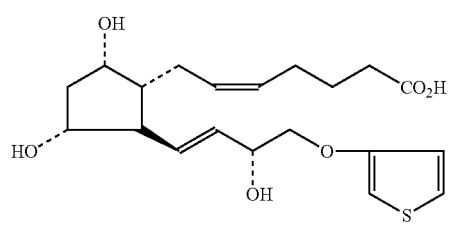

For the top compound (I), R=H, $C_{1-4}$ alkyl, or $H_2HC(CH_2OH)_3$; $R^1$, $R^2$=H or Me; and $R^3$=a heterocycle (often substituted).

U.S. Pat. No. 4,055,602 discloses several compounds such as the one shown below,

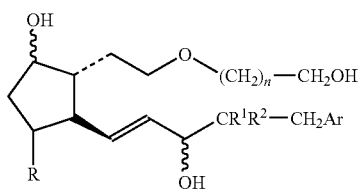

wherein n=2-4; R=H or OH; $R^1$, $R^2$=H, F, Me; and Ar=aryl. The '602 patent also discloses the compound shown below, and others like it.

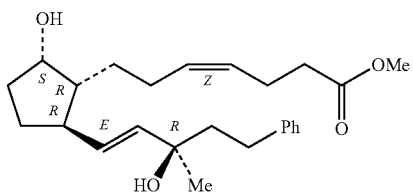

DE 2626888 discloses several compounds such as the one shown below.

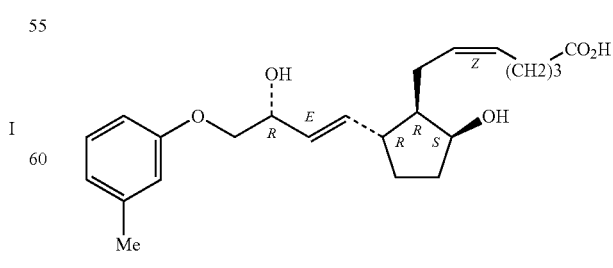

Other references, such as U.S. Pat. No. 4,119,727, disclose similar compounds.

BRIEF DESCRIPTION OF THE INVENTION

A compound comprising

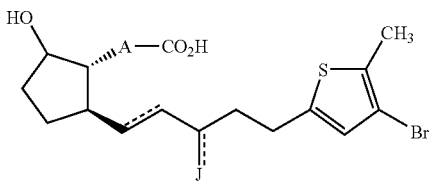

or a pharmaceutically acceptable salt, or a prodrug thereof;

wherein the dashed line indicates the presence or absence of a bond;

A is —(CH$_2$)$_6$—, or cis —CH$_2$—CH=CH—(CH$_2$)$_3$—, wherein 1 or 2 carbons may be substituted with S or O;

J is —OH or =O;

or a pharmaceutically acceptable salt or a prodrug thereof, is disclosed herein.

Also disclosed herein are compounds having an α and an ω chain comprising

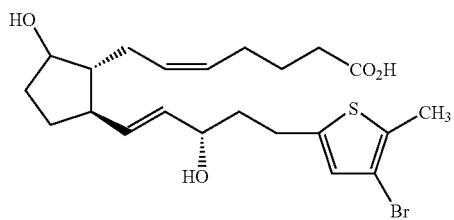

or a derivative thereof, wherein said derivative has a structure as shown above except that 1 or 2 alterations are made to the α chain and/or the ω chain, and wherein an alteration consists of:
a. adding, removed, or substituting a non-hydrogen atom, or
b. changing the bond order of an existing covalent bond without adding or deleting said bond;

or a pharmaceutically acceptable salt, a tetrazole, or a prodrug thereof.

Also disclosed herein are methods of treating diseases or conditions, including glaucoma and elevated intraocular pressure. Compositions and methods of manufacturing medicaments related thereto are also disclosed.

BRIEF DESCRIPTION OF THE DRAWING FIGURES

Figure 2:
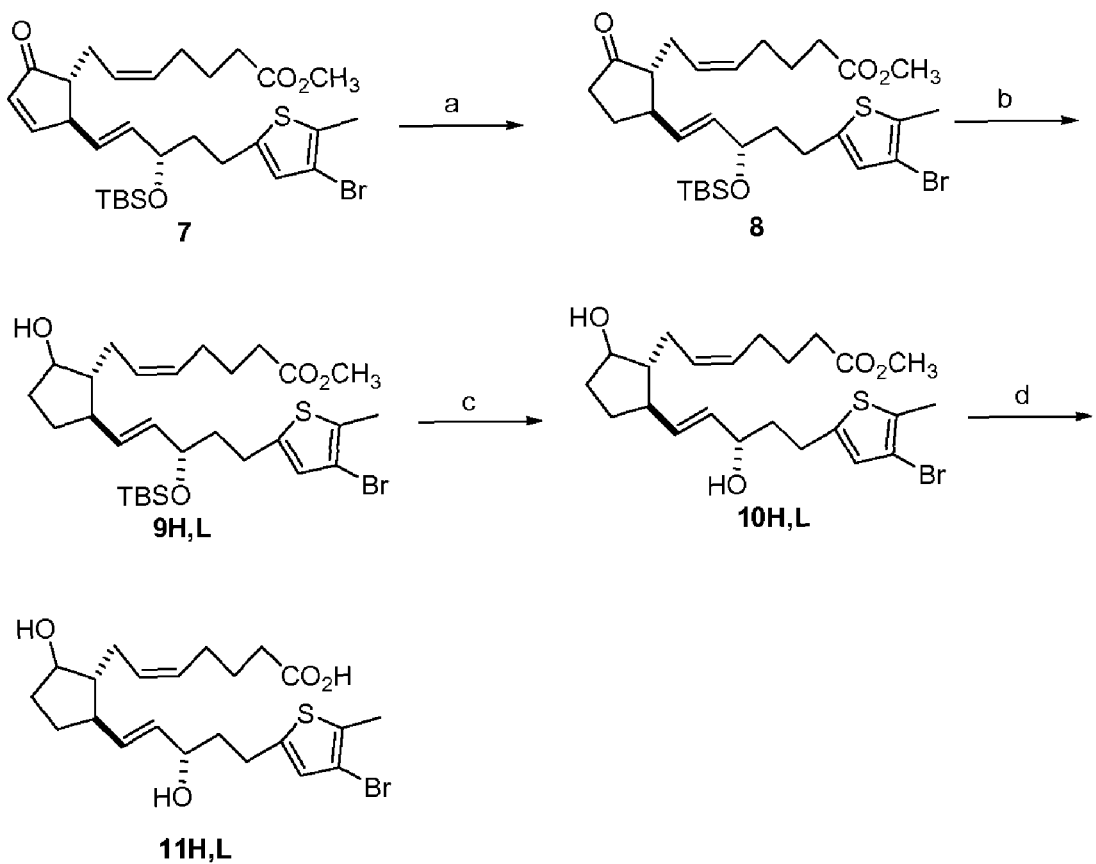

FIGS. 1 and 2 illustrate one method of preparing the compounds disclosed herein.

DETAILED DESCRIPTION OF THE INVENTION

A person of ordinary skill in the art understands the meaning of the stereochemistry associated with the hatched wedge/ solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, indicated as a "dashed line", "represents a bond receding from the viewer."

In relation to the identity of A disclosed in the chemical structures presented herein, in the broadest sense, A is —(CH$_2$)$_6$—, or cis —CH$_2$CH=CH—(CH$_2$)$_3$—, wherein 1 or 2 carbons may be substituted with S or O. In other words, A may be —(CH$_2$)$_6$—, cis —CH$_2$CH=CH—(CH$_2$)$_3$—, or A may be a group which is related to one of these two moieties in that any carbon is substituted with S or O. For example, while not intending to limit the scope of the invention in any way, A may be an S substituted moiety such as one of the following or the like.

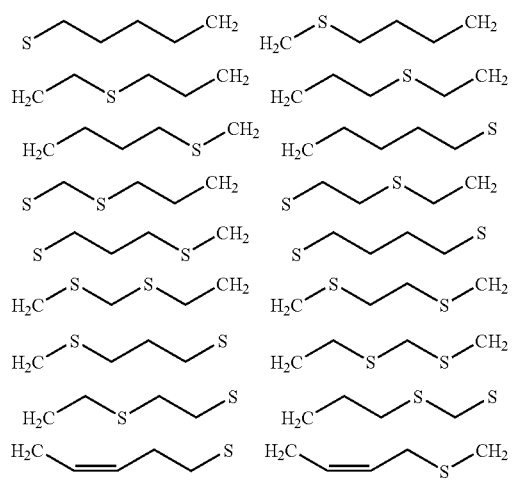

Alternatively, while not intending to limit the scope of the invention in any way, A may be an O substituted moiety such as one of the following or the like.

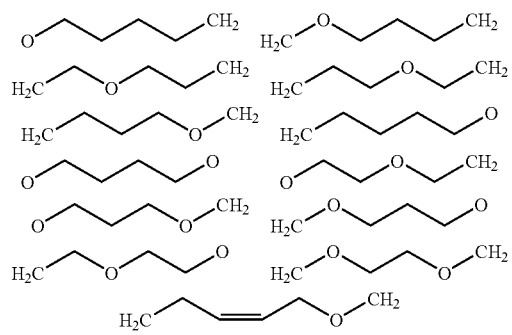

In other embodiments, A is —(CH$_2$)$_6$— or cis—CH$_2$CH=CH—(CH$_2$)$_3$— having no heteroatom substitution.

Since J can be —OH or =O, compounds of the structures shown below are possible, or pharmaceutically acceptable salts or prodrugs thereof.

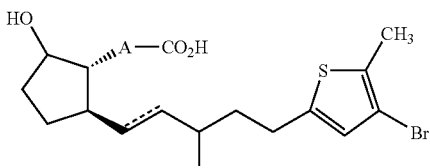

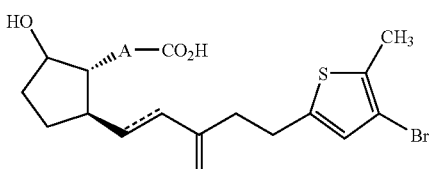

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Ester prodrugs of the compounds disclosed herein are specifically contemplated. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

A "tetrazole" as disclosed herein is meant to be a compound wherein a carboxylic acid is substituted with a tetrazole functional group. Thus, a tetrazole of a compound of the structure

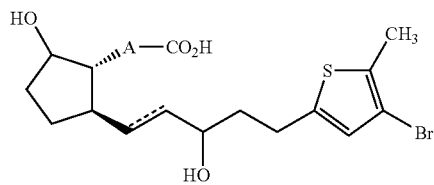

would have the structure shown below.

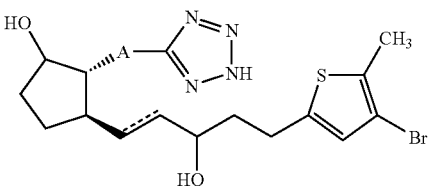

Tetrazoles are known in the art to be interchangeable with carboxylic acids in biological systems. In other words, if a compound comprising a carboxylic acid is substituted with a tetrazole, it is expected that the compound would have similar biological activity. A pharmaceutically acceptable salt or a prodrug of a tetrazole is also considered to be a tetrazole for the purposes of this disclosure.

Another embodiment comprises

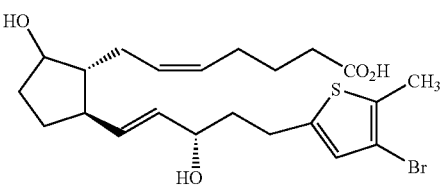

or a pharmaceutically acceptable salt, a tetrazole, or a prodrug thereof. In other embodiments, the compound is the acid or a pharmaceutically acceptable salt, and not a tetrazole or a prodrug.

Another embodiment comprises

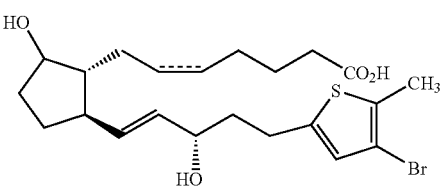

or a pharmaceutically acceptable salt, a tetrazole, or a prodrug thereof. In other embodiments, the compound is the acid or a pharmaceutically acceptable salt, and not a tetrazole or a prodrug.

One embodiment comprises derivatives of

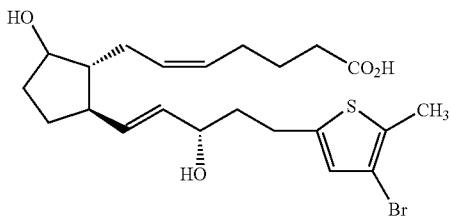

wherein said derivative has a structure as shown above except that 1 or 2 alterations are made to the α chain and/or the ω chain, wherein an alteration consists of 1) adding, removed, or substituting a non-hydrogen atom, or 2) changing the bond order of an existing covalent bond without adding or deleting said bond. Salts, tetrazoles, and prodrugs of the depicted compound or derivatives thereof are also contemplated.

Thus, a compound having the structure above is contemplated, as well as a pharmaceutically acceptable salt a prodrug, or a tetrazole thereof.

In making reference to a derivative and alterations to a structure as shown above, it should be emphasized that making alterations and forming derivatives is strictly a mental exercise used to define a set of chemical compounds, and has nothing to do with whether said alteration can actually be carried out in the laboratory, or whether a derivative can be prepared by an alteration described. However, whether the derivative can be prepared via any designated alteration or not, the differences between the derivatives and the aforementioned structure are such that a person of ordinary skill in the art could prepare the derivatives disclosed herein using routine methods known in the art without undue experimentation.

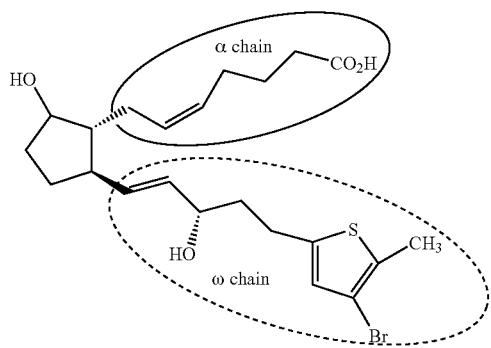

The α chain is the group in the solid circle in the labeled structure above. The ω chain is the group in the dashed circle in the labeled structure above. Thus, in these embodiments said derivative may be different from the formula above at the α chain, while no alteration is made to the ω chain, as for example, in the structures shown below.

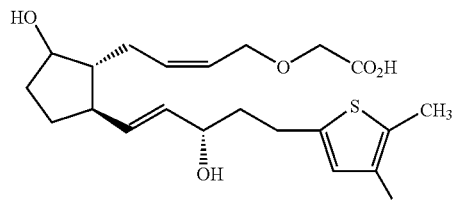

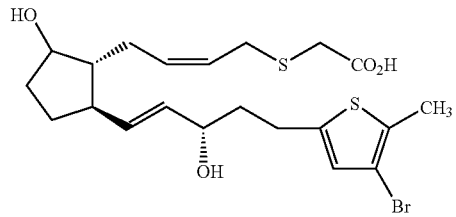

Pharmaceutically acceptable salts, tetrazoles, and prodrugs of these compounds are also contemplated.

The derivatives may also be different from the formula above in the ω chain, while no alteration is made to the α chain, as shown in the examples below.

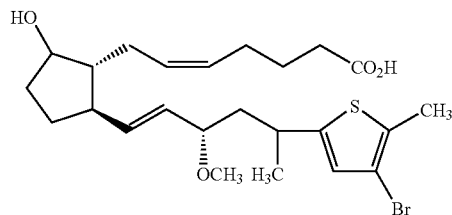

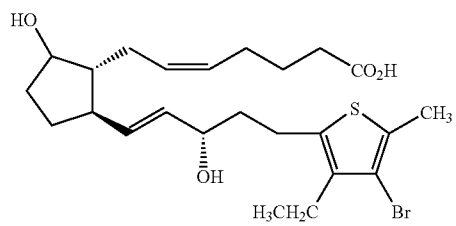

Pharmaceutically acceptable salts, tetrazoles, and prodrugs of these compounds are also contemplated.

Alternatively, the derivatives may be different in both the α and ω chains, as shown in the examples below.

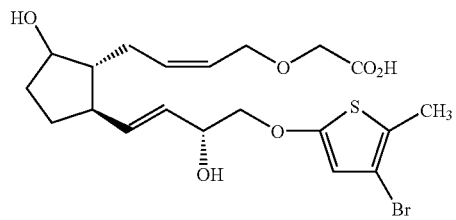

-continued

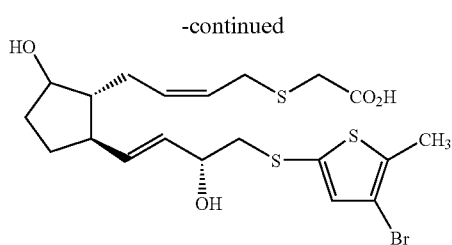

Pharmaceutically acceptable salts, tetrazoles, and prodrugs of these compounds are also contemplated.

Changes to the structure can take several forms, if a non-hydrogen atom is added, the structure is changed by adding the atom, and any required hydrogens, but leaving the remaining non-hydrogen atoms unchanged, such as in the two examples shown below, with the added atoms in bold type.

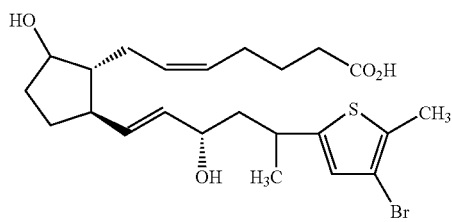

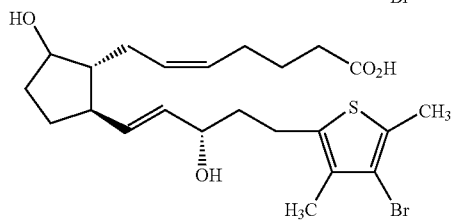

Pharmaceutically acceptable salts, tetrazoles, and prodrugs of these compounds are also contemplated.

If a non-hydrogen atom is removed, the structure is changed by removing the atom, and any required hydrogens, but leaving the remaining non-hydrogen atoms unchanged, such as in the two examples shown below, with the previous location of the missing atoms indicated by arrows.

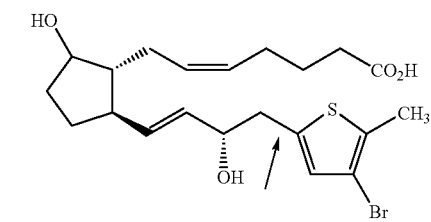

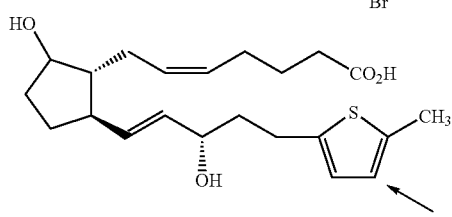

Pharmaceutically acceptable salts, tetrazoles, and prodrugs of these compounds are also contemplated.

If a non-hydrogen atom is substituted, the non-hydrogen atom is replaced by a different non-hydrogen atom, with any necessary adjustment made to the number of hydrogen atoms, such as in the two examples shown below, with the substituted atoms in bold type.

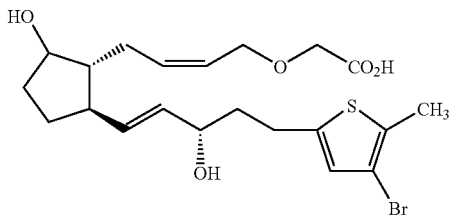

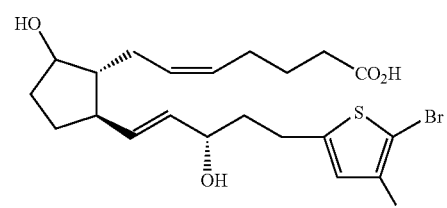

Pharmaceutically acceptable salts, tetrazoles, and prodrugs of these compounds are also contemplated.

Changing the bond order of an existing covalent bond without adding or deleting said bond refers to the changing of a single bond to a double or triple bond, changing a double bond to a single bond or a triple bond, or changing a triple bond to a double or a single bond. Adding or deleting a bond, such as occurs when an atom is added, deleted, or substituted, is not an additional alteration for the purposes disclosed herein, but the addition, deletion, or substitution of the non-hydrogen atom, and the accompanying changes in bonding are considered to be one alteration. Three examples of this type of alteration are shown below, with the top two examples showing alteration in the double bond of the α chain, and the bottom example showing alteration in the C—O single bond of the ω chain.

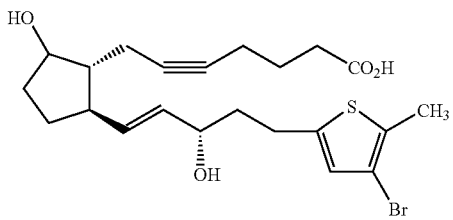

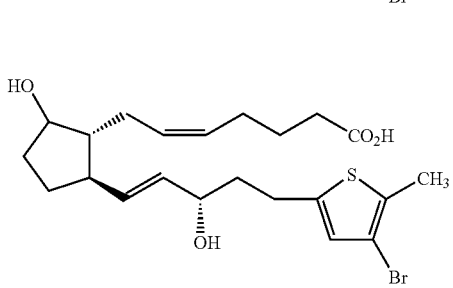

-continued

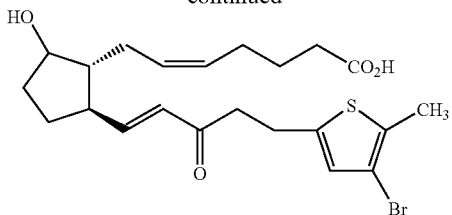

Pharmaceutically acceptable salts, tetrazoles, and prodrugs of these compounds are also contemplated.

If a derivative could reasonably be construed to consist of a different number of alterations, the derivative is considered to have the lowest reasonable number of alterations. For example, the compound shown below, having the modified portion of the molecule in bold, could be reasonably construed to have 1 or 2 alterations relative to the defined structure.

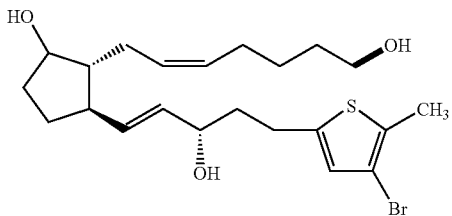

By one line of reasoning, the first alteration would be to remove the hydroxyl group from the carboxylic acid functional group, yielding an aldehyde. The second alteration would be to change the C=O double bond to a single bond, yielding the alcohol derivative shown above. By a second line of reasoning, the derivative would be obtained by simply removing the carbonyl oxygen of the carboxylic acid to yield the alcohol. In accordance with the rule established above, the compound above is defined as having 1 alteration. Thus, an additional alteration could be made to the structure to obtain the compounds such as the examples shown below.

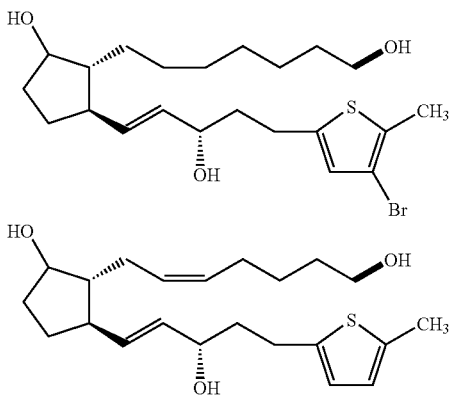

Pharmaceutically acceptable salts, tetrazoles, and prodrugs of these compounds are also contemplated.

In one embodiment, O or S is substituted for $CH_2$, as seen in several of the examples disclosed previously herein, as well as in the examples below.

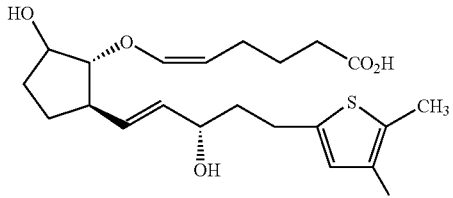

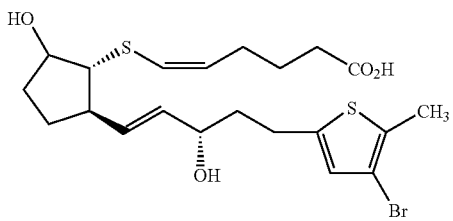

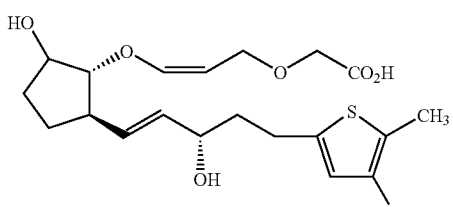

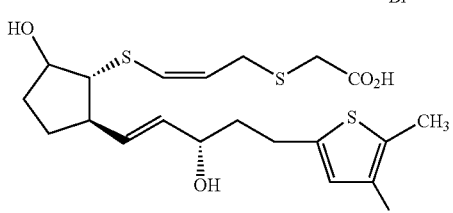

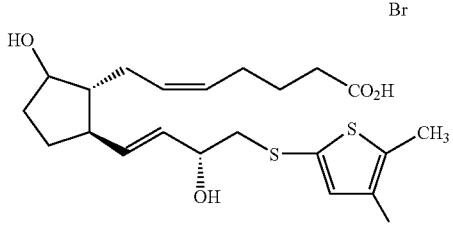

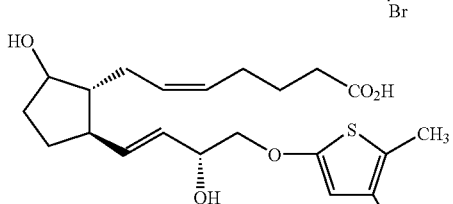

Pharmaceutically acceptable salts, tetrazoles, and prodrugs of these compounds are also contemplated.

Certain compounds comprise C=O, i.e. the bond order of the C—O bond is increased from a single to double bond as in the compounds shown below.

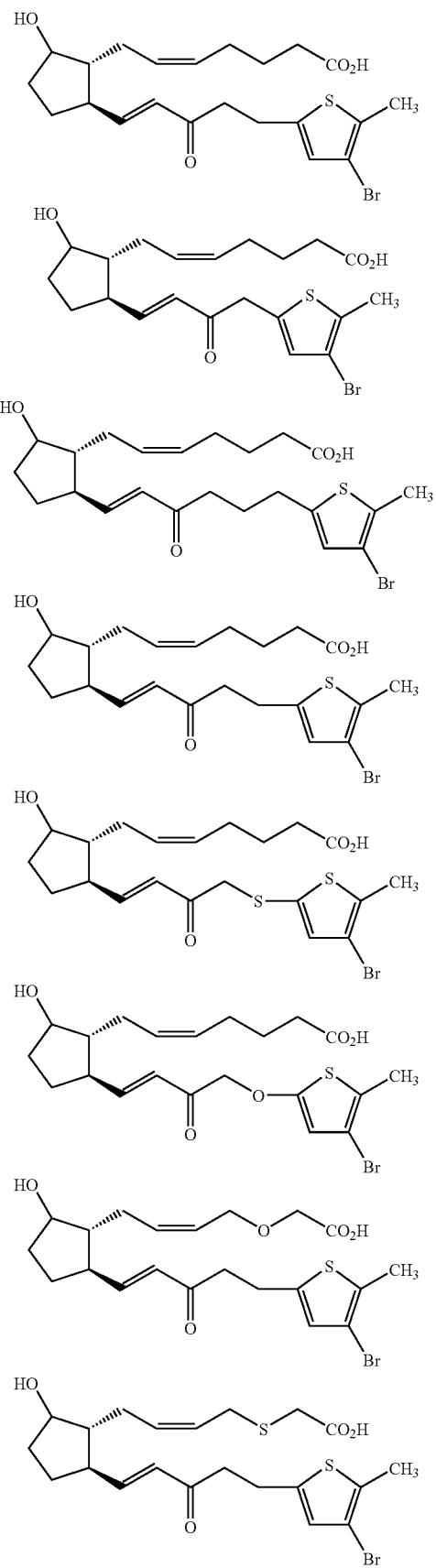
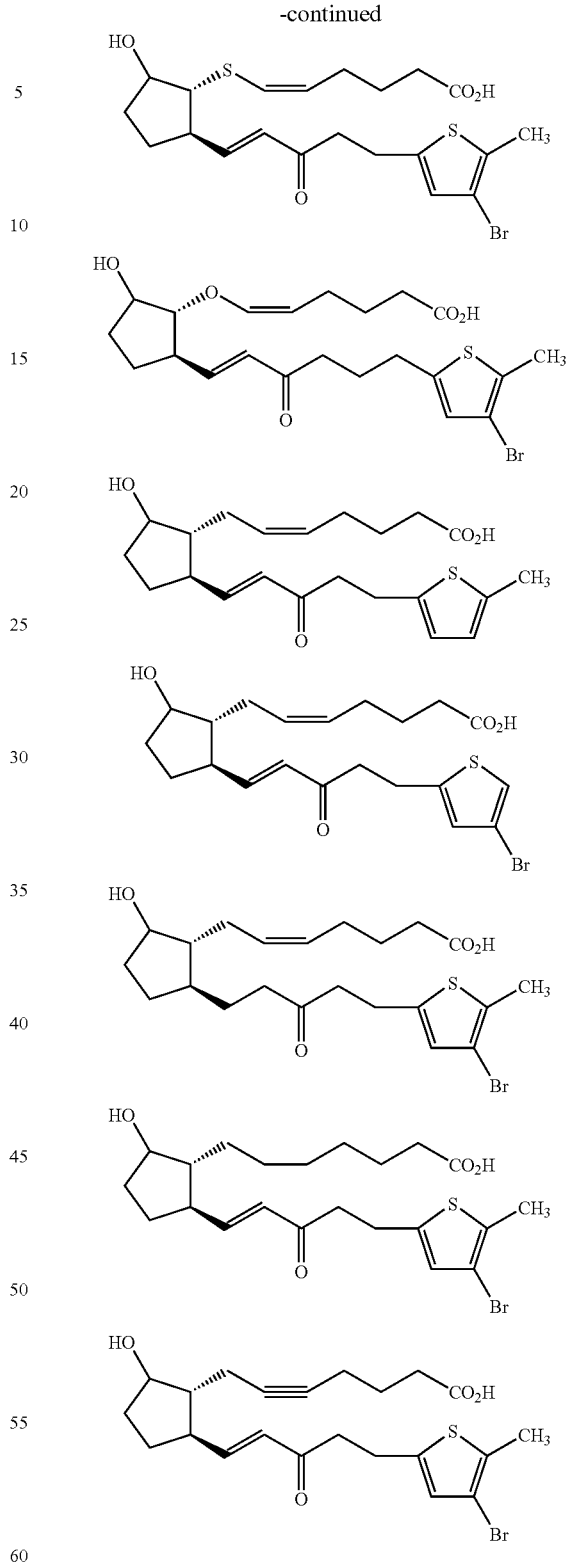
Pharmaceutically acceptable salts, tetrazoles, and prodrugs of these compounds are also contemplated.
Other embodiments comprise no Br, i.e. it is removed or another atom is substituted for it, as in the examples shown below.

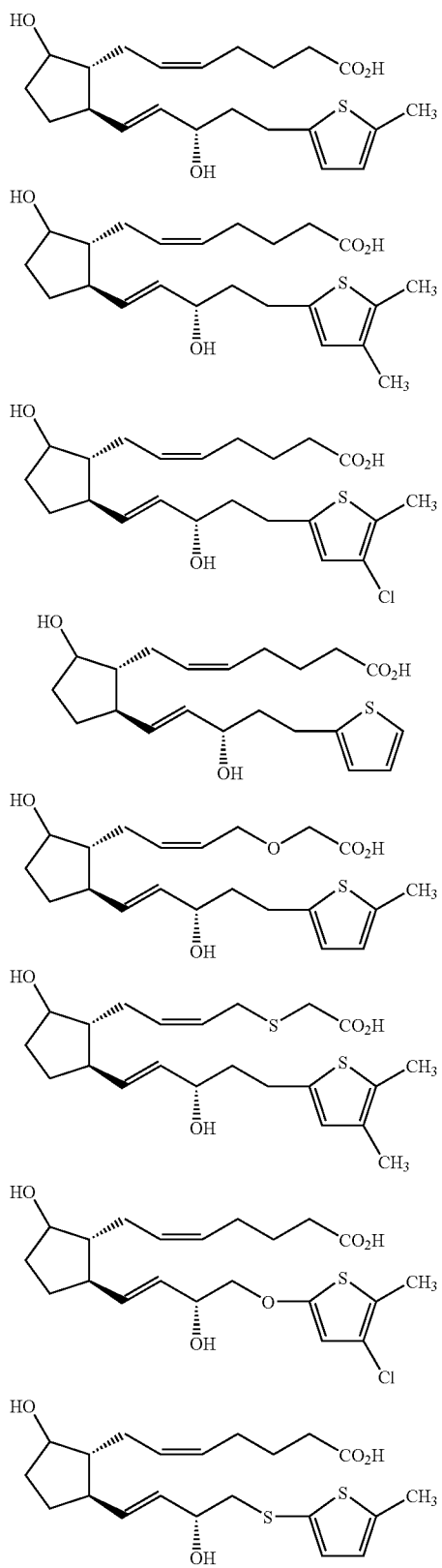
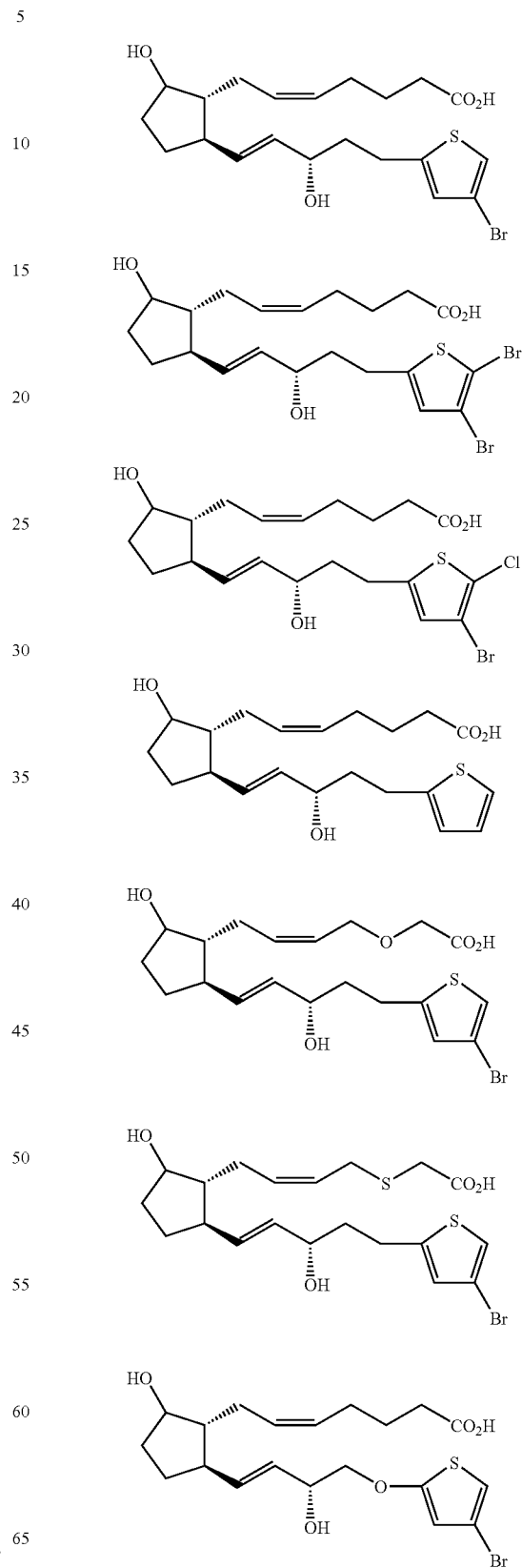
Other embodiments comprise no $CH_3$, i.e. it is removed or another atom is substituted for it, as in the examples shown below.
Pharmaceutically acceptable salts, tetrazoles, and prodrugs of these compounds are also contemplated.

-continued

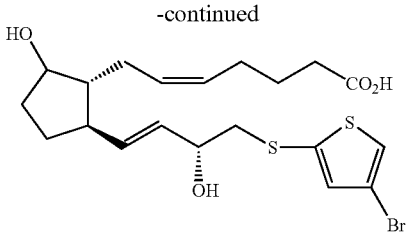

Pharmaceutically acceptable salts, tetrazoles, and prodrugs of these compounds are also contemplated.

In many embodiments, the compound comprises a thienyl or substituted thienyl moiety. A number of examples of these compounds are given above. However, certain embodiments may have a substituted furyl, phenyl, or other aromatic moiety, such as the examples shown below.

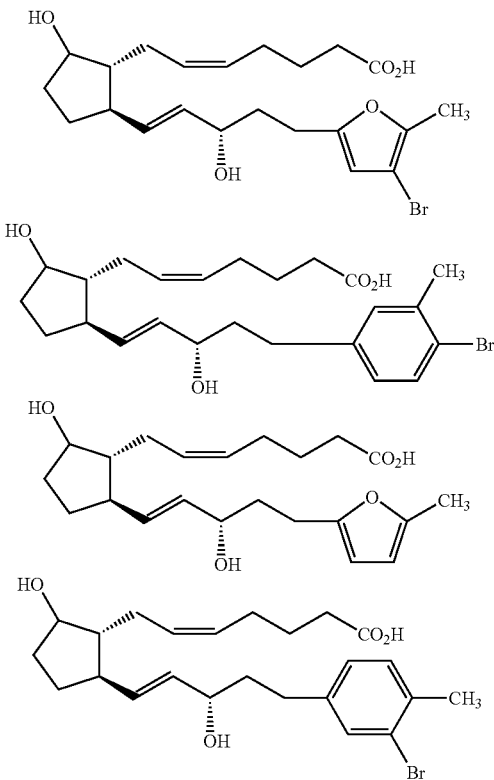

Pharmaceutically acceptable salts, tetrazoles, and prodrugs of these compounds are also contemplated.

Another embodiment comprises (Z)-7-{(1R,2R)-2-[(E)-(S)-5-(4-Bromo-5-methyl-thiophen-2-yl)-3-hydroxy-pent-1-enyl]-5-hydroxy-cyclopentyl}-hept-5-enoic acid.

The compounds of disclosed herein are useful for the prevention or treatment of glaucoma or ocular hypertension in mammals, or for the manufacture of a medicament for the treatment of glaucoma or ocular hypertension.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric, acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

Example 1

Compounds of Table 1 were prepared according to the following procedures.

Compound 1 was prepared by methods disclosed in U.S. Pat. No. 6,124,344, incorporated by reference herein.

(Z)-7-[(1R,2R,3R,5S)-2-[(E)-(S)-5-(4-Bromo-5-methyl-thiophen-2-yl)-3-(tetrahydro-pyran-2-yloxy)-pent-1-enyl]-3,5-bis-(tetrahydro-pyran-2-yloxy)-cyclopentyl]-hept-5-enoic acid methyl ester (2)

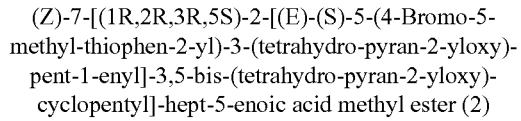

An acetone (24 mL) solution of acid 1 was treated with DBU (1.4 mL, 9.36 mmol) and methyl iodide (0.6 mL, 9.63 mmol). The reaction was stirred for 21 h and then 50 mL 1 M HCl was added and the mixture extracted with ethyl acetate (3×50 mL). The combined ethyl acetate solution was dried (Na$_2$SO$_4$), filtered and evaporated to leave a brown oil that was used directly in the next step.

(Z)-7-{(1R,2R,3R,5S)-2-[(E)-(S)-5-(4-Bromo-5-methyl-thiophen-2-yl)-3-hydroxy-pent-1-enyl]-3,5-dihydroxy-cyclopentyl}-hept-5-enoic acid methyl ester (3)

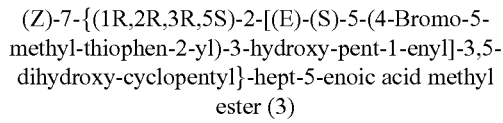

A mixture of the crude ester (2) in methanol (16 mL) was treated with pyridinium p-toluenesulfonate (2.625 g, 10.4 mmol). After 21 h, the solvent was evaporated in vacuo and the residue purified by flash chromatography on silica gel (90% ethyl acetate/hexanes→95%) to give 3 (3.453 g, 6.9 mmol, 86% for the two steps).

(Z)-7-[(1R,2R,3R,5S)-2-[(E)-(S)-5-(4-Bromo-5-methyl-thiophen-2-yl)-3-(tert-butyl-dimethyl-silanyloxy)-pent-1-enyl]-3-(tert-butyl-dimethyl-silanyloxy)-5-hydroxy-cyclopentyl]-hept-5-enoic acid methyl ester (4)

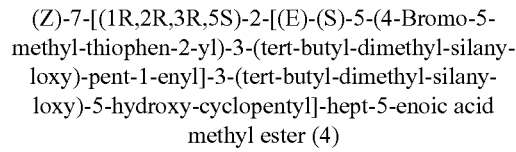

A dichloromethane (14 mL) solution of 3 (3.452 g, 6.9 mmol) was treated with triethylamine (2.9 mL, 20.8 mmol), DMAP (211 mg, 1.73 mmol) and TBSCl (2.130 g, 14.1 mmol). The reaction was allowed to stir for 22 h and then was quenched by addition of 100 mL saturated NaHCO$_3$ solution. The mixture was extracted with CH$_2$Cl$_2$ (3×75 mL) and the combined CH$_2$Cl$_2$ solution was dried (Na$_2$SO$_4$), filtered and evaporated. Purification by flash chromatography (10% ethyl acetate/hexane→20%) gave 4 (3.591 g, 4.9 mmol, 71%).

(Z)-7-[(1R,2R,3R)-2-[(E)-(S)-5-(4-Bromo-5-methyl-thiophen-2-yl)-3-(tert-butyl-dimethyl-silanyloxy)-pent-1-enyl]-3-(tert-butyl-dimethyl-silanyloxy)-5-oxo-cyclopentyl]-hept-5-enoic acid methyl ester (5)

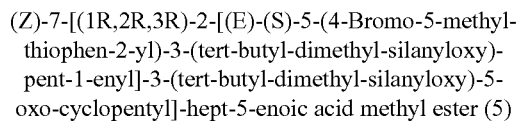

A mixture of alcohol 4 (3.591 g, 4.9 mmol), 4A molecular sieves (2.5 g), and NMO (867 mg, 7.4 mmol) in dichloromethane (10 mL) was treated with TPAP (117 mg, 0.33 mmol). After 1 h, the mixture was filtered through celite and the filtrate evaporated in vacuo. Purification by flash chromatography (5% ethyl acetate/hexanes→7.5%) gave 5 (2.984 g, 4.1 mmol, 84%).

(Z)-7-{(1R,2S)-2-[(E)-(S)-5-(4-Bromo-5-methyl-thiophen-2-yl)-3-hydroxy-pent-1-enyl]-5-oxo-cyclopent-3-enyl}-hept-5-enoic acid methyl ester (6)

A mixture of 5 (1.486 g, 2.03 mmol), HOAc (20 mL), $H_2O$ (10 mL) and THF (10 mL) was stirred at 70° C. for 17 h. The reaction was then poured into 750 mL saturated $NaHCO_3$ solution and the resulting mixture was extracted with ethyl acetate (4×200 mL). The combined ethyl acetate solution was dried ($Na_2SO_4$), filtered and evaporated. Flash chromatography (50% ethyl acetate/hexanes) gave 6 (497 mg, 1.03 mmol, 51%).

(Z)-7-{(1R,2S)-2-[(E)-(S)-5-(4-Bromo-5-methyl-thiophen-2-yl)-3-(tert-butyl-dimethyl-silanyloxy)-pent-1-enyl]-5-oxo-cyclopent-3-enyl}-hept-5-enoic acid methyl ester (7)

A dichloromethane (6 mL) solution of 6 (497 mg, 1.03 mmol) was treated with 2,6-lutidine (143 µL, 1.22 mmol) and TBSOTf (0.26 mL, 1.13 mmol). After 1.5 h, 50 mL saturated $NaHCO_3$ was added and the resulting mixture was extracted with 25 mL $CH_2Cl_2$. The $CH_2Cl_2$ layer was washed with 50 mL 1 M HCl and 50 mL brine. The $CH_2Cl_2$ solution was then dried ($Na_2SO_4$), filtered and evaporated. Purification by flash chromatography (8% ethyl acetate/hexanes→10%) gave 7 (553 mg, 0.93 mmol, 90%).

(Z)-7-{(1R,2R)-2-[(E)-(S)-5-(4-Bromo-5-methyl-thiophen-2-yl)-3-(tert-butyl-dimethyl-silanyloxy)-pent-1-enyl]-5-oxo-cyclopentyl}-hept-5-enoic acid methyl ester (8)

A solution of 7 (170 mg, 0.28 mmol) in 4 mL toluene was added, by cannula, to a −40° C. mixture of hydrido(triphenylphosphine)copper(I) hexamer (300 mg, 0.15 mmol) in 4 mL toluene, rinsing with 0.5 mL toluene. The temperature was allowed to warm to 0° C. over 1 h and then was allowed to warm to room temperature. After a further 1 h, the reaction was quenched by addition of 15 mL saturated $NH_4Cl$ solution. The mixture was extracted with ethyl acetate (3×15 mL) and the combined ethyl acetate solution was dried ($Na_2SO_4$), filtered and evaporated. Purification by flash chromatography (8% ethyl acetate/hexanes→10%) gave the title ketone (150 mg, 0.25 mmol, 89%).

(Z)-7-{(1R,2R)-2-[(E)-(S)-5-(4-Bromo-5-methyl-thiophen-2-yl)-3-(tert-butyl-dimethyl-silanyloxy)-pent-1-enyl]-5-hydroxy-cyclopentyl}-hept-5-enoic acid methyl ester (9H,L)

A methanol (0.8 mL) solution of ketone 8 (150 mg, 0.25 mmol) was treated with $NaBH_4$ (15 mg, 0.40 mmol). After 1 h, the reaction was quenched with 15 mL 1 M HCl and the resulting mixture was extracted with dichloromethane (3×15 mL). The combined dichloromethane solution was dried ($Na_2SO_4$), filtered and evaporated to give the alcohols 9H,L which were used directly in the next step.

(Z)-7-{(1R,2R)-2-[(E)-(S)-5-(4-Bromo-5-methyl-thiophen-2-yl)-3-hydroxy-pent-1-enyl]-5-hydroxy-cyclopentyl}-hept-5-enoic acid methyl ester (10H,L)

A solution of the crude alcohols 9 in HOAc (2 mL)/$H_2O$ (1 mL)/THF (1 mL) was heated at 70° C. for 2 h and then was quenched by addition of 100 mL saturated $NaHCO_3$ solution. The resulting mixture was extracted with ethyl acetate (4×100 mL) and the combined ethyl acetate solution was dried ($Na_2SO_4$), filtered and evaporated. Flash chromatography (45% ethyl acetate/hexanes) followed by preparative TLC (42% ethyl acetate/hexanes) gave the two C9 diastereomers: high $R_f$ 29 mg (0.06 mmol, 24% for 2 steps) and low $R_f$ 53 mg (0.11 mmol, 43%).

(Z)-7-{(1R,2R)-2-[(E)-(S)-5-(4-Bromo-5-methyl-thiophen-2-yl)-3-hydroxy-pent-1-enyl]-5-hydroxy-cyclopentyl}-hept-5-enoic acid (11H)

A THF (1.3 mL) solution of 10H (27 mg, 0.055 mmol) was treated with 0.5 M LiOH (0.33 mL, 0.17 mmol). The reaction was allowed to stir for 18 h and then 10 mL 1 M HCl was added. The resulting mixture was extracted with dichloromethane (3×15 mL) and the combined dichloromethane solution was dried ($Na_2SO_4$), filtered and evaporated. Purification by flash chromatography (5% methanol/dichloromethane) gave 11H (20 mg, 0.042 mmol, 77%). 300 MHz NMR ($CDCl_3$, ppm) δ 6.58 (1H, s) 5.6-5.3 (4H, overlapping m) 4.3-4.1 (2H, overlapping m) 2.8-2.7 (2H, m) 2.32 (3H, s) 2.4-1.3 (16H, overlapping m).

TABLE 1

| | | FUNCTIONAL DATA (EC50 nm) | | | | | | | |
|---|---|---|---|---|---|---|---|---|---|
| Rf | STRUCTURE | HFP | HEP1 | HEP2 | HEP3A | HEP4 | HTP | HIP | HDP |
| High | | 2069 | NA | NA | >10⁵ | NA | 1868 | NA | NA |

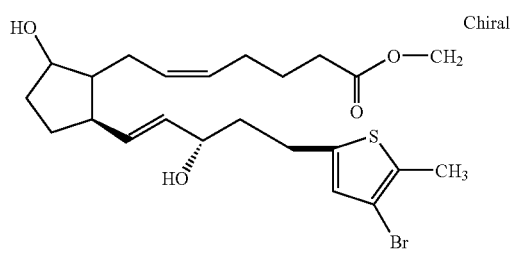

TABLE 1-continued

| Rf | STRUCTURE | | HFP | HEP1 | HEP2 | HEP3A | HEP4 | HTP | HIP | HDP |
|---|---|---|---|---|---|---|---|---|---|---|
| Low | (structure) | Chiral | NA | NA | NA | NA | NA | NA | NA | NA |
| High | (structure) | Chiral | >$10^5$ | NA | 793 | >$10^5$ | 96 | NA | NA | |
| Low | (structure) | Chiral | >$10^5$ | NA | NA | >$10^5$ | 832 | >$10^5$ | NA | NA |

Example 2

The biological activity of the compounds of Table 1 was tested using the following procedures.

Methods for FLIPR™ Studies (a) Cell Culture

HEK-293 (EBNA) cells, stably expressing one type or subtype of recombinant human prostaglandin receptors (prostaglandin receptors expressed: hDP/Gqs5; hEP$_1$; hEP$_2$/Gqs5; hEP$_{3a}$/Gqi5; hEP$_4$/Gqs5; hFP; hIP; hTP), were cultured in 100 mm culture dishes in high-glucose DMEM medium containing 10% fetal bovine serum, 2 mM 1-glutamine, 250 µg/ml geneticin (G418) and 200 µg/ml hygromycin B as selection markers, and 100 units/ml penicillin G, 100 µg/ml streptomycin and 0.25 µg/ml amphotericin B.

(b) Calcium Signal Studies on the FLIPR™

Cells were seeded at a density of 5×$10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 µM, plates were washed four times with HBSS-HEPES buffer to remove excess dye leaving 100 µl in each well. Plates were re-equilibrated to 37° C. for a few minutes.

Cells were excited with an Argon laser at 488 nm, and emission was measured through a 510-570 nm bandwidth emission filter (FLIPR™, Molecular Devices, Sunnyvale, Calif.). Drug solution was added in a 50 µl volume to each well to give the desired final concentration. The peak increase in fluorescence intensity was recorded for each well. On each plate, four wells each served as negative (HBSS-HEPES buffer) and positive controls (standard agonists: BW245C (hDP); PGE$_2$ (hEP$_1$; hEP$_2$/Gqs5; hEP$_{3,4}$/Gqi5; hEP$_4$/Gqs5); PGF$_{2\alpha}$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$ M. The duplicate values were averaged. In either, HTS or CoRe format each compound was tested on at least 3 separate plates using cells from different passages to give an n≧3.

The results of the activity studies presented in the table demonstrate that the compounds disclosed herein are prostaglandin receptor agonists, and are thus useful for the treatment of glaucoma, ocular hypertension, the other diseases or conditions related to the activity of the prostaglandin receptors.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof, rather, the ambit of the present invention is to be governed only by the lawful construction of the appended claims.

What is claimed is:

1. A method for treating glaucoma or elevated intraocular pressure comprising administering to a subject in need thereof a therapeutically effective amount of a composition comprising one or more excipients and a compound, wherein the composition is an ophthalmically acceptable liquid, and wherein said compound has the structure

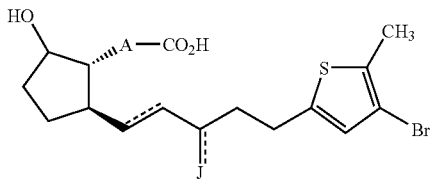

or a pharmaceutically acceptable salt thereof;
wherein the dashed line indicates the presence or absence of a bond;
A is —(CH$_2$)$_6$—, or cis —CH$_2$—CH=CH—(CH$_2$)$_3$—, wherein 1 or 2 carbons may be substituted with S or O;
J is —OH or =O.

2. The method of claim 1, wherein said compound has the structure

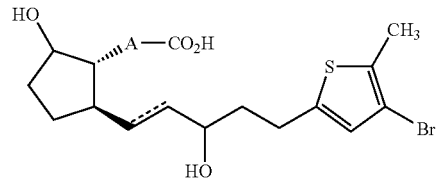

or a pharmaceutically acceptable salt thereof.

3. The method of claim 1, wherein said compound has the structure

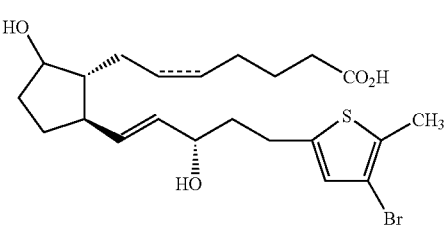

or a pharmaceutically acceptable salt thereof.

4. The method of claim 1, wherein said compound has the structure

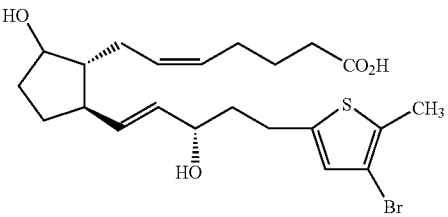

or a pharmaceutically acceptable thereof.

* * * * *